United States Patent [19]

Adelberg

[11] Patent Number: 5,014,962
[45] Date of Patent: May 14, 1991

[54] CLAMP FOR REGULATING FLUID FLOW THROUGH PLASTIC TUBING

[76] Inventor: Marvin Adelberg, 16821 Oak View Dr., Encino, Calif. 91436

[21] Appl. No.: 318,129

[22] Filed: Mar. 2, 1989

[51] Int. Cl.$^5$ .............................................. F16K 7/06
[52] U.S. Cl. ......................................................... 251/6
[58] Field of Search ......................................... 251/6, 4

[56] References Cited

U.S. PATENT DOCUMENTS

| | | | |
|---|---|---|---|
| 3,477,686 | 11/1969 | Engelsher et al. | 251/10 |
| 3,685,787 | 8/1972 | Adelberg | 251/6 |
| 3,893,468 | 7/1975 | McPhee | 251/6 |
| 3,918,675 | 11/1975 | Forberg | 251/6 |
| 4,013,263 | 3/1977 | Adelberg | 251/6 |
| 4,047,694 | 9/1977 | Adelberg | 251/6 |
| 4,340,201 | 7/1982 | Becker, Jr. | 251/6 |
| 4,475,709 | 10/1984 | Becker, Jr. | 251/6 |
| 4,725,037 | 2/1988 | Adelberg | 251/6 |

Primary Examiner—John Rivell
Assistant Examiner—L. R. Leo
Attorney, Agent, or Firm—Edward A. Sokolski

[57] ABSTRACT

Tubing through which fluid flow is to be regulated is placed in a regulating clamp wherein it is clamped between a roller wheel and a surface which is substantially parallel to the travel of the wheel. The surface has a variable cross-sectional area channel extending within or therealong. Flow rate through the tubing is changed by longitudinal adjustment of the position of the roller wheel, the ratio between the portion of the tubing which is clamped shut to that which is exposed to the channel, and consequently not being clamped, thereby being varied. A plurality of raised elements are formed in the surface and act to locally pinch or grip the tubing at discrete intervals thereby both improving the grip and lessening the creep of the tubing. The raised element which is most remote from the channel is substantially higher than the raised element closer to the channel to provide a more constant flow rate especially with thicker and harder walled tubing.

10 Claims, 3 Drawing Sheets

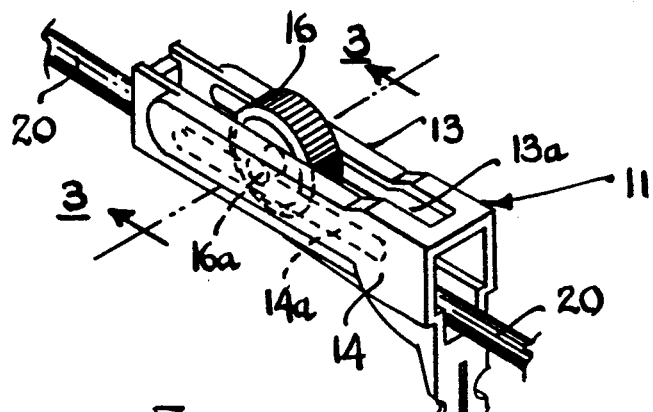
Fig. 2
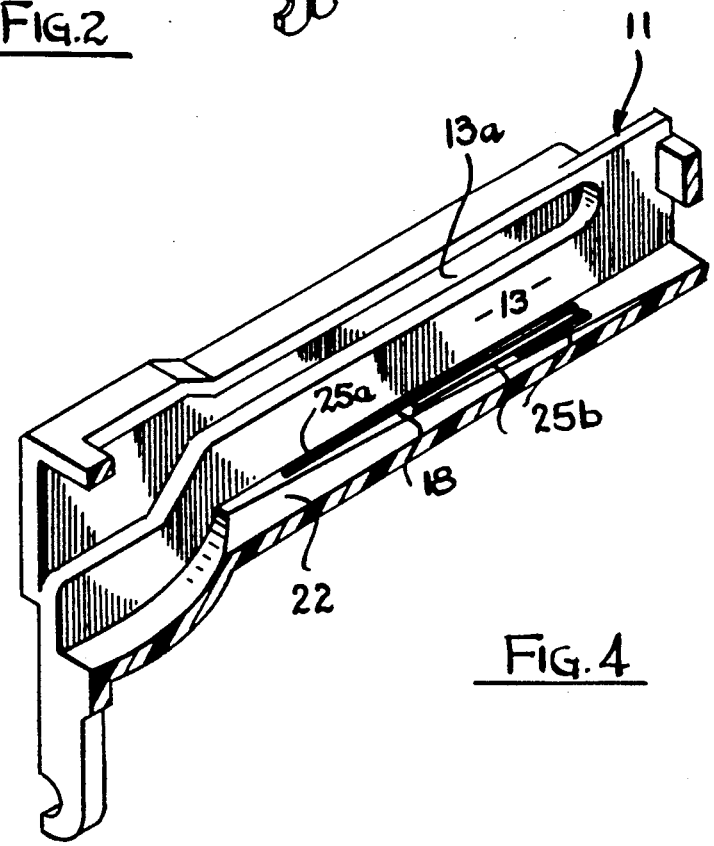
Fig. 4
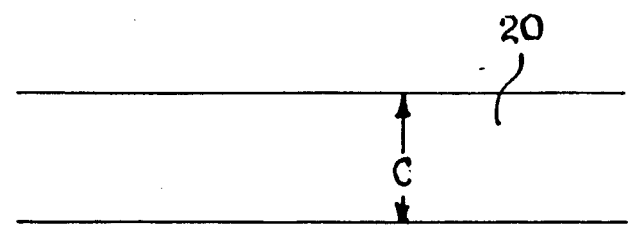
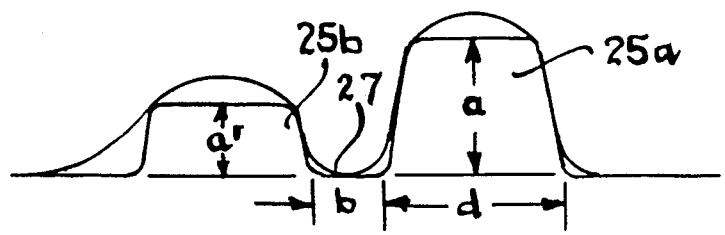
Fig. 6

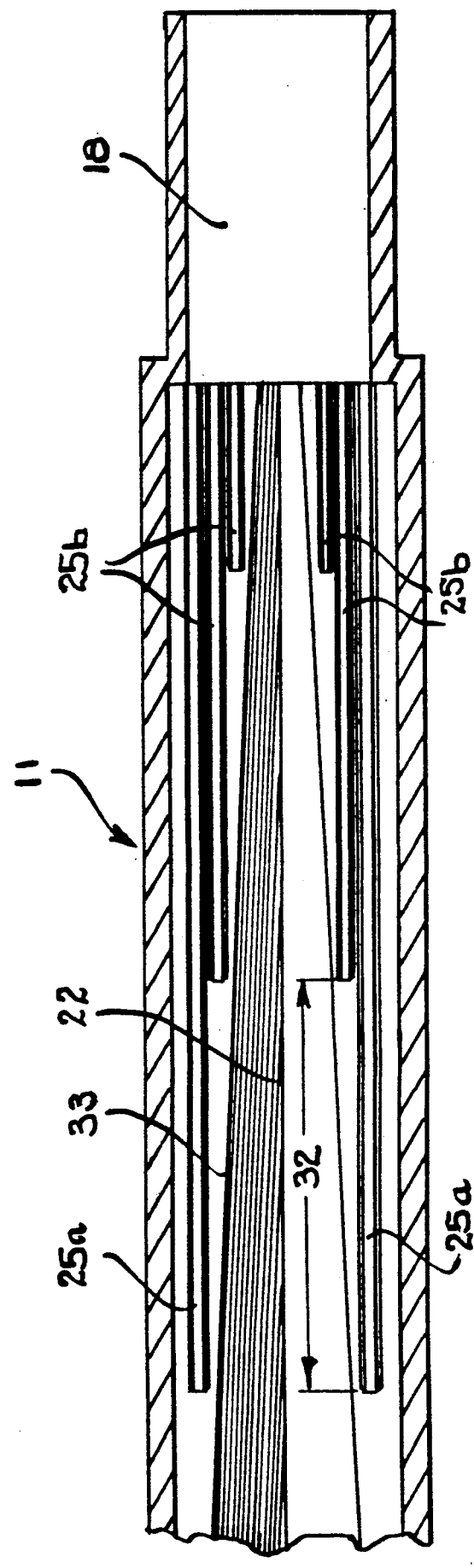

CLAMP FOR REGULATING FLUID FLOW THROUGH PLASTIC TUBING

BACKGROUND OF THE INVENTION

1. FIELD OF THE INVENTION

This invention relates to clamping devices for use in regulating fluid flow through plastic tubing and more particularly to such a device employing a roller wheel which is adjusted along a generally longitudinal axis relative to an opposing clamping surface, to adjust and set the fluid flow rate through the tubing.

2. DESCRIPTION OF THE PRIOR ART

In my U.S. Pat. Nos. RE 31,584, 4,013,263, 4,047,694 and 4,725,037, clamping devices are described for regulating fluid flow through plastic tubing which are particularly useful in the administration of parenteral fluids. The clamps of my aforementioned patents have the advantage in that creep or cold flow of the plastic material of the tubing is greatly reduced to provide a more constant rate of flow of the parenteral solution diminishing the need for later adjustment once an initial setting has been made. In my U.S. Pat. Nos. 4,013,263, 4,047,694 and 4,725,037 clamps are described in which an improvement in the constancy of the flow rate is achieved by employing raised portions formed in the clamping surface which portions are separated from each other by discrete valley portions so as to pinch or grip the tubing in discrete locations or intervals, thereby substantially lessening creep of the plastic and minimizing flow rate changes once the clamp has been set for the desired flow rate. In the preferred embodiments of these patents, the raised portions are in the form of long ridges which are spaced from each other in an optimum manner for creep reduction.

Generally, softer tubing acts in a more compliant manner when combined with a pinch clamp because such tubing will more readily conform to the new configuration imposed by the clamp. Harder or stiffer tubing has the attractive feature of being resistant to kinking when coiled or bent as is the case when packaged. Kinking may be defined as a permanent deformation assumed by a tube due to a radical and/or long term new configuration imposed to cause the tube to assume a new configuration with a radius of curvature below some critical value. Plastic tubing when used as a disposable assembly for intravenous feeding is often packaged in the shape of a compact oblong coil. The coil is approximately 8 inches long and 3 inches wide while the tube is some 70 inches long. If the coil radius is too small, the tube will tend to kink, thus compromising the tube's ability to transfer fluids when later put to use. Large radius coils are undesirable because the coils occupy too large a volume when being stored prior to use. Thus, stiffer tubing is considered as a means to make possible a compact tube coil package. Increased stiffness may be achieved by a thicker wall cross section or by increasing the hardness of the tubing material, or both.

A thicker walled tubing usually helps to reduce the tendency for the tube to kink.

When utilizing a generally parallel acting clamp, at any given tubing cross section, a portion of the tubing must be fully pinched shut as well as being tightly confined. Utilizing a thicker wall or stiffer tubing tends to make the problem of pinching and confining more difficult by requiring the pinch clamp to be stronger and larger in size so as to provide additional force and leverage, respectively. Furthermore, the small raised elements on the housing clamping surface such as those described in U.S. Pat. No. 4,013,353 may be less effective with tubing having stiffer and/or thicker walls.

Furthermore, for the case of stiffer and/or thicker walled tubing, introduction of the raised elements tends to have an effect upon the size of the lumen formed, generally tending to increase its size, (other things being equal).

In one series of controlled experiments, it was observed that the effective flow cross section of the formed lumens was considerably greater when raised elements were introduced and all other factors were unchanged. This difference was even more dramatic when tubing which was both stiffer and having a thicker wall was used in the study. In that application, the market required that this type of stiff, thicker walled tubing be used and would not permit the introduction of a thinner walled softer tubing.

In a second controlled study, it was observed that when the raised elements were located closer to the relief section of the clamping surface of the clamp housing, the effective lumen cross section was larger, than when the raised element nearest the relief section was more distant.

Having the raised element more distant from the relief section of the clamping surface reduced the size of the lumen, but this did not offer the full benefit of the raised elements (tug resistance and improved flow control).

SUMMARY OF THE INVENTION

The clamp of the present invention provides an improvement in operation particularly where thicker or harder walled tubing is employed with which the clamps of my prior patents having ridges formed in the clamping surface tend to provide a less constant flow rate than with thinner or softer tubing.

The clamp of the present invention while providing the advantages of my prior clamps employing ridges such as that shown in FIG. 1, avoids the aforementioned shortcomings of such clamps especially when used with thicker and harder walled tubing, and also offers an improvement when used with thinner or softer walled plastic tubing.

Briefly this improved end result is obtained by tailoring the geometry of the ridges so that the ridges closer to the relief groove in or adjacent the clamping surface have a substantially lesser height than those further from the groove. The higher raised elements such as those employed in the prior art, provide the desired local gripping and pinch isolation to the plastic tubing while the lesser height elements added in the present improvement and located closer to the relief groove provide moderate local gripping while not greatly altering the tube configuration. At least one lesser height element is placed near the relief groove while at least one higher element is placed in a generally more remote location from the groove. The remote higher raised element or elements has a height and spacing, the optimum dimensions of which are related to the tube wall thickness. The shorter elements have a height and spacing which is determined by the tube wall thickness and/or hardness of the tubing.

It is therefore an object of the invention to improve the operation of a tubing clamp having gripping ridges in the clamping surface expecially but not exclusively where used with harder or thicker wall tubing.

Other objects of the invention will become apparent as the description proceeds in connection with accompanying drawings of which:

DESCRIPTION OF DRAWINGS

FIG. 2 is a perspective view illustrating a preferred embodiment of the present invention;

FIG. 4 is a perspective view with partial cut-away sections illustrating the preferred embodiment;

FIG. 5 is a top cross sectional view of the preferred embodiment; and

FIG. 6 is a schematic view illustrating the dimensional relationships of the raised portions of the preferred embodiment.

DESCRIPTION OF INVENTION

Figure 1:
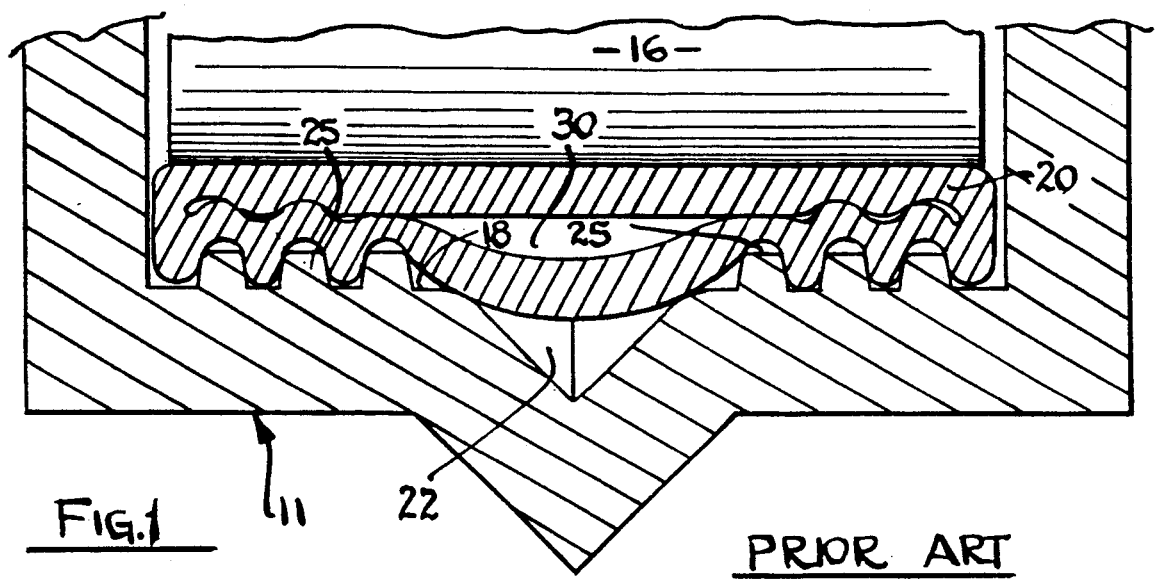
FIG. 1 is a cross sectional drawing illustrating the operation of a prior art clamp.
Figure 3:
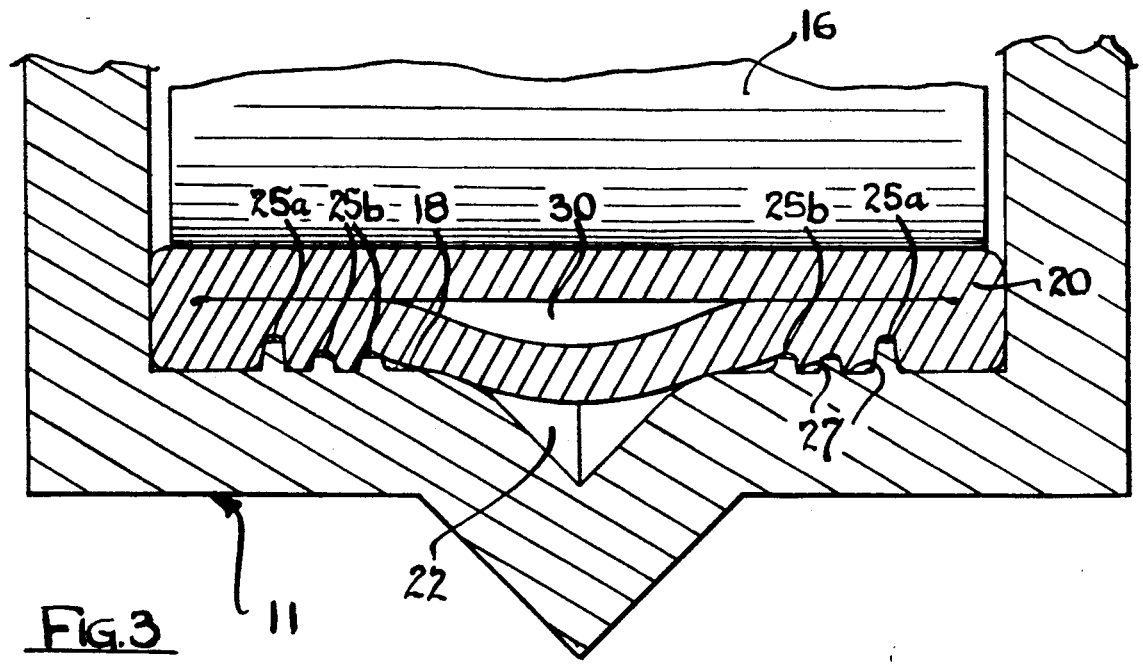
FIG. 3 is a cross sectional view taken along the plane indicated by FIG. 3—3 in FIG. 2.

Referring now to the FIGS. 2 through 6, a preferred embodiment of the invention is illustrated. The preferred embodiment of the clamp of the present invention differs from the preferred embodiment of that of my prior U.S. Pat. No. 4,013,263 only insofar as the clamping surface 18 is concerned. The clamp has a body portion or housing 11 having side walls 13 and 14 with oppositely positioned trunnion grooves 13a and 14a formed therein. Roller wheel 16 has a pair of trunnions (one of which 16a is shown in FIG. 2) extending therefrom which ride in grooves 13a and 14a respectively. The body of the clamp also has a bottom surface 18 which serves as a clamping surface against which plastic tubing 20 is clamped by wheel 16. Formed in the central part of surface 18 is a variable width and variable depth channel 22. Clamping surface 18 is substantially parallel to grooves 13a and 14a such that the separation distance between wheel 16 and surface 18 remains substantially constant throughout the travel of the wheel on its trunnions. The flow rate of fluid through tubing 20 is adjusted to the desired value by positioning wheel 16 along grooves 13a and 14a, whereby the tubing is compressed fully shut against surfaces which are adjacent to desired portions of the channel having varying depths and widths at a desired station of the wheel. The device thus far described is similar to the preferred embodiment of my aforementioned U.S. Pat. No. 4,013,263 and reference to that patent may be made for any additional descriptive details of the structure and operation of the device as thus far described.

The preferred embodiment of the present invention as illustrated in FIGS. 2 through 6 is involved with the special tailored geometry of raised portions or ridges 25a and 25b formed in clamping surface 18 as compared with the raised portions 25 of the prior art, all of which in this case may have approximately the same height. Raised portions 25a and 25b are separated from each other by discrete valley portions 27. In the preferred embodiment of this invention, raised portions 25a and 25b are made substantially parallel to the longitudinal axis of the clamp body to facilitate the manufacturing; however, they could also run in other directions and be a series of interrupted elements or ridges of equal or unequal length or width. While six of such ridge elements have been shown, the number of such elements can vary for different application requirements but at least two on each side of the channel 22 are required. The raised elements 25a which are most remote from channel 22 and separated from channel 22 over some of its length by at least one raised element are substantially taller or higher than raised elements 25b which are closer to such channel. The tops of raised elements or ridges 25a and 25b are preferably rounded which will provide a good grip on the tubing and effectively lessen creep without damaging the tubing as sharp edge ridges might.

Remote raised elements 25a provide the desired local gripping for the plastic tubing while the shorter elements 25b which are closer to channel 22 provide moderate local gripping while not as greatly altering the configuration of the control lumen 30 which is formed by comparison with the clamp of the prior art shown in FIG. 1 which has raised elements 25 generally all of the same height. As best can be seen in FIG. 6, the remote raised elements 25a have a height "a" which is of the order of the compressed wall thickness "c" of tubing 20. Raised elements 25b which are closer to groove have a height a' which is in the range of 0.2-0.8 of that of elements 25a with a preferred height of approximately 0.5 of the height "a" of the remote raised elements, The width "d" of all of the raised elements as well as the spacing "b" therebetween are in the range of $\frac{1}{2}$-3 times the height "a" of elements 25a.

As can be seen in FIG. 5, where groove 22 is relatively narrow, approaching the "shut-off" zone, there are two pairs of lower ridges 25b and only one pair of higher ridges 25a while in the region where the groove 22 is wider, there is only one pair of each of the lower ridges 25b and higher ridges 25a.

Because of practical molding problems, the preferred embodiment has raised elements 25a, 25b parallel to the travel of the wheel and not parallel to the edge 33 of the tapered relief groove 22. Thus, in that portion 32 of the clamping surface where the tapered relief groove approaches its maximum width there may be only a single raised element adjacent to the relief groove edge. In this particular region, the features of the present invention are not utilized. However, the clamp as is the case with other prior art clamps as well, is normally designed with marginal operating zones which are utilized very infrequently, such as when the tube is unintentionally out of the specified size range or an unusually large or small flow restriction is elsewhere in the fluid flow path. Normally, the active zone of the clamp is in the central portion (as is usually the case with many other prior art clamps). Well before the wheel reaches its "full shut off" mechanical extreme there is a zone where no fluid flow takes place. This is because the relief groove in this zone is too small to create a lumen under normal conditions. At the other extreme, well before the wheel reaches its "maximum flow" position, there is range of travel of the wheel where the actual flow is unchanged with change of wheel position. This is usually because one or more elements in the fluid path limit the flow rate when the wheel is near its "wide open position". This element in the fluid path could be a drip orifice or a small bore catheter. In the extreme high flow range of the clamp, which in practice is rarely utilized to maintain a uniform flow rate, only the prior art designs can be utilized because in this region there is only one raised element adjacent the edge of the tapered relief groove. For the practice of the present invention, two or more raised elements to at least one side of the relief groove are required.

While the preferred embodiment of the invention shows the groove 22 in the center and the ridges 25a and 25b on opposite sides of the groove, the invention may also be implemented in a device where the groove is to one side such as shown in patent no. U.S. Pat. No. 3918675. In such case, the ridges would all be on one side of the groove.

While the invention has been described and illustrated in detail, it is to be clearly understood that this intended by way of illustration and example only and is not to be taken by way of limitation, the spirit and scope of the invention being limited only by the terms of the following claims.

I claim:

1. In a clamp for regulating fluid flow through plastic tubing having a body portion with a longitudinal clamping surface, a variable cross-section longitudinal channel being formed in or along said surface, a roller wheel mounted in said body for longitudinal motion substantially parallel to said surface and a plurality of distributed raised elements separated from each other by discrete valley portions formed in said clamping surface for locally gripping the tubing wall at given locations thereby restraining the tubing so as to reduce creep thereof, the tubing being clamped between the roller wheel and said surface, the improvement comprising:

at least two of said raised elements being on one side of the channel, at least one of said raised elements most remote from said channel having a height substantially greater than the raised element closer to said channel, thereby to provide a more constant and controlled flow rate especially with thicker and harder walled tubing.

2. The clamp of claim 1 wherein said one of said raised elements most remote from said channel has a height of the order of the compressed wall thickness of said tubing and said raised element closer to said channel has a height which 0.2–0.8 of that of said one of said elements.

3. The clamp of claim 1 wherein said raised elements comprise ridges which run substantially parallel to the longitudinal axis of the body portion of the clamp, there being at least one of said most remote raised elements and at least one of said closer elements on said one side of said channel.

4. The clamp of claim 3 wherein the width and spacing between the raised elements is ⅓–3 times the height of said most remote raised element.

5. The clamp of claim 1 wherein the height of the raised element closer to said channel is approximately 0.5 of the raised element most remote from said channel.

6. The clamp of claim 1 wherein there are at least three raised elements on each side of said channel, the raised element most remote from said channel having a length greater than that of the other raised elements.

7. The clamp of claim 6 wherein the other raised elements include one raised element adjacent at least a portion of said channel and another raised element located between said one raised element most remote from said channel and the raised element adjacent said channel.

8. The clamp of claim 1 wherein the raised element most remote from said channel has a length greater than the other of the raised elements.

9. The clamp of claim 1 wherein the raised element closest to said channel has a length which is less than that of the raised element most remote from said channel.

10. The clamp of claim 2 wherein there is more than one raised element on each side of said channel.

* * * * *